(12) United States Patent
DeMayo

(10) Patent No.: US 6,416,518 B1
(45) Date of Patent: Jul. 9, 2002

(54) COMBINED SURGICAL DRILL AND SURGICAL SCREW GUIDE

(75) Inventor: Edward N. DeMayo, San Raphael, CA (US)

(73) Assignee: IMP Inc., Plainville, CT (US)

( * ) Notice: Subject to any disclaimer, the term of this patent is extended or adjusted under 35 U.S.C. 154(b) by 0 days.

(21) Appl. No.: 09/900,726

(22) Filed: Jul. 9, 2001

(51) Int. Cl.[7] ................................ A61B 17/56

(52) U.S. Cl. .................. 606/96; 606/80; 606/98

(58) Field of Search ................ 606/96, 73, 232, 606/104, 72, 80, 98, 69

(56) References Cited

U.S. PATENT DOCUMENTS

| 4,341,206 | A | * | 7/1982 | Perret et al. | 606/96 |
| 5,993,451 | A | * | 11/1999 | Burkhart | 606/73 |
| 6,013,083 | A | * | 1/2000 | Bennet | 606/104 |
| 6,120,511 | A | * | 9/2000 | Chan | 606/96 |
| 6,210,415 | B1 | * | 4/2001 | Bester | 606/96 |
| 6,254,605 | B1 | * | 7/2001 | Howell | 606/96 |
| 6,287,313 | B1 | * | 9/2001 | Sasso | 606/96 |

* cited by examiner

*Primary Examiner*—Pedro Philogene

(57) ABSTRACT

A combined surgical drill and screw guide utilizes a common support cylinder for first guiding the drill guide and then guiding the screw with no auxiliary screw guide insert required. The interior diameter of the cylinder is sized for clearance of the head portion of the screw

3 Claims, 2 Drawing Sheets

COMBINED SURGICAL DRILL AND SURGICAL SCREW GUIDE

BACKGROUND OF THE INVENTION

Surgical screws are widely used in orthopedic surgery to fix broken bones as well as to maintain the broken bones in alignment during the healing process.

A surgical drill guide, such as described in U.S. Pat. No. 5,047,034 entitled "Intramedullary Rod Screw Guide", describes the use of a drill guide tube for holding and guiding a drill bit for drilling a passage in the bone, and a screw guide tube for holding and guiding a surgical screw within the passage.

U.S. Pat. No. 4,537,185 entitled "Cannulated Fixation Screw" describes an earlier arrangement of a hollow self-tapping surgical screw that is placed over a guide pin mounted in a guide pin hole in a bone to drill and tap a hole at a predetermined location in the bone.

U.S. Pat. No. 5,147,367 entitled "Drill Pin Guide and Method for Orthopedic Surgery" describes a later application of a guide pin, a drill guide and a surgical screw for the fixation of a bone fracture.

In view of the strict antiseptic requirements of the operating room sterile field, it would be advantageous to use a minimum amount of surgical equipment when inserting one or more surgical screws during an orthopedic bone repair procedure.

One purpose of the instant invention is to describe apparatus and methods for holding and guiding a surgical drill and a surgical screw with the minimum amount of apparatus necessary to drill a bone and to insert a surgical screw therein.

SUMMARY OF THE INVENTION

A combined surgical drill and screw guide utilizes a common support cylinder for first guiding the drill guide and then guiding the screw with no auxiliary screw guide insert required. The support cylinder includes a handle attached thereto for allowing manual manipulation of the support cylinder during the insertion of the cylinder end within the bone as well as allowing manual support during the drilling and screwing operations. The interior diameter of the cylinder is sized for clearance of the head portion of the screw.

DESCRIPTION OF THE PREFERRED EMBODIMENT

Figure 1:
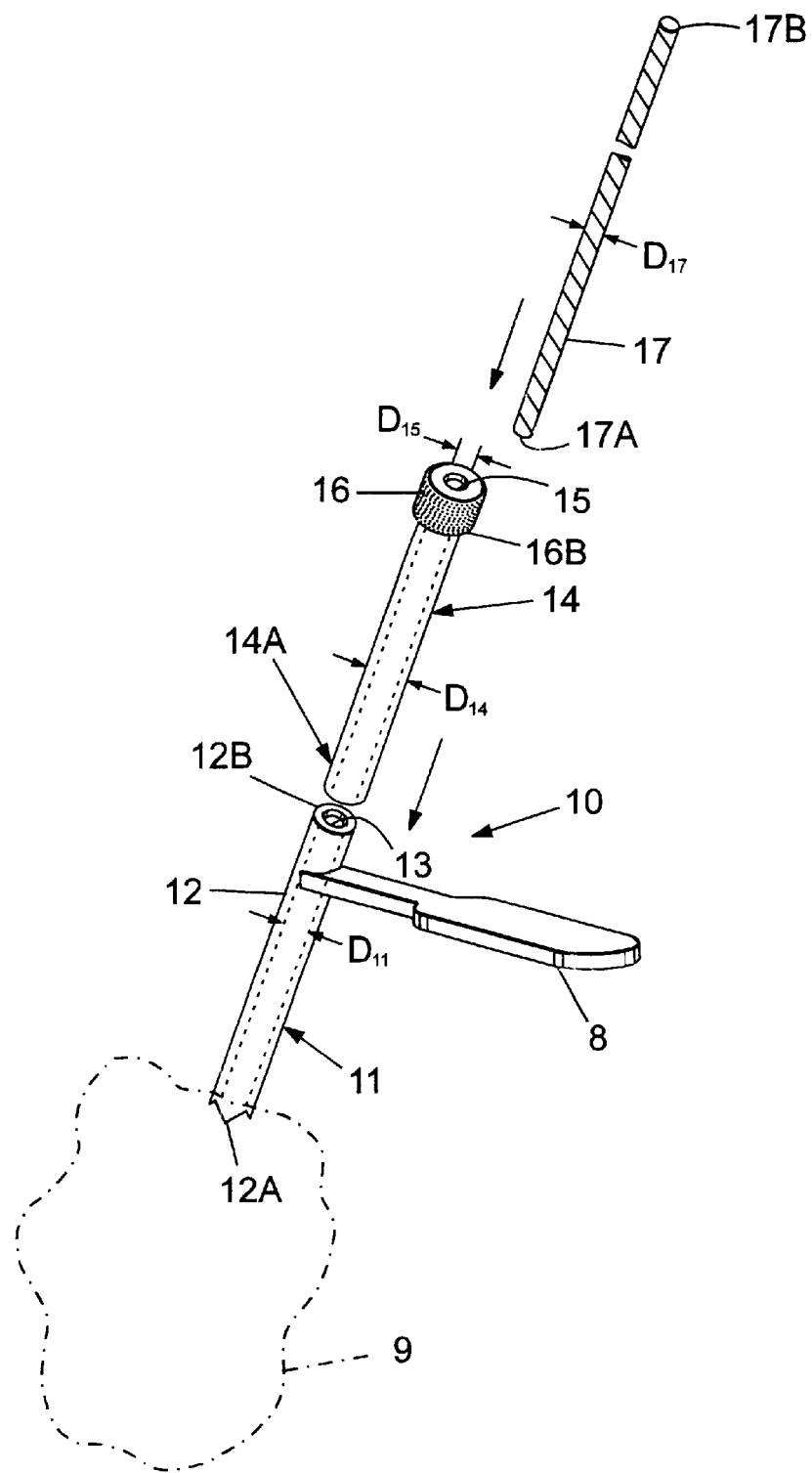
FIG. 1 is a top perspective view of the combined drill and screw guide of the invention with the drill and drill guide in isometric projection.

The combined drill and screw guide 10 of the invention is shown in FIG. 1 and includes a cannula 11 of cylindrical configuration 12 defining a bottom serrated end 12A, for perforating the surface of a bone 9 upon rotation of the handle 8 extending from the top part of the cannula, and a top cylindrical end 12B defining an opening 13 for receiving the end 14A of the drill guide 14 having an external diameter D14. The drill guide 14 is inserted within the cannula 11 such that the internal diameter D11 of the cannula is sized for clearance relation with the outer diameter D14 of the drill guide 14.

The opposite end 14B of the drill guide includes a knurled cap 16 with an internal opening 15 of diameter D15. A drill 17 having a bottom pointed end 17A for penetrating the bone 9 and a top cylindrical end 17B for engagement with a drill chuck. The outer diameter D17 of the drill 17 is sized for clearance relation with the internal diameter D15 of the internal opening 15 of the drill guide 14. The arrangement of the drill guide 14 within the cannula 11, and the positioning of the drill 17 within the drill guide-cannula assembly thereby allows controlled rotation of the drill to provide an accurate drill hole within the bone 9.

Figure 2:
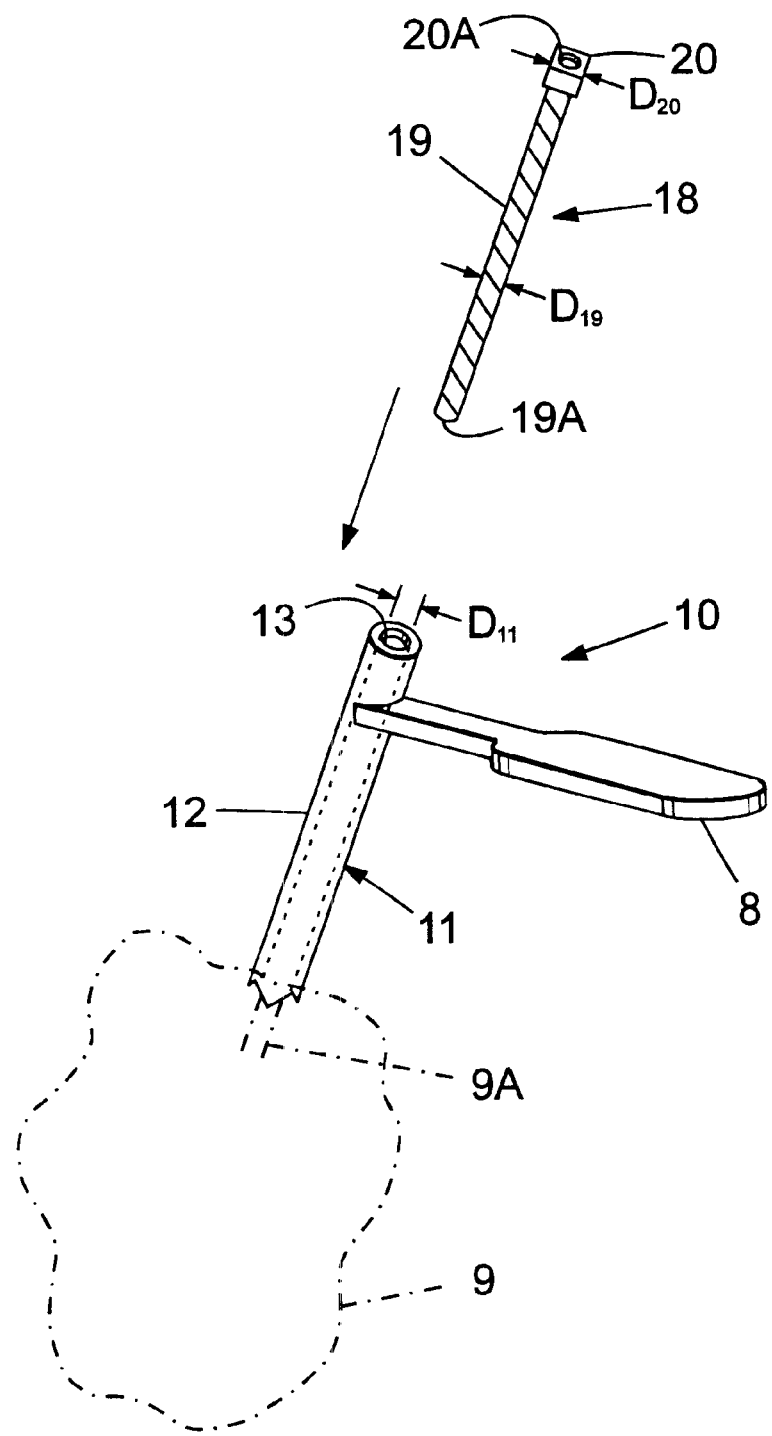
FIG. 2 is a top perspective view of the combined drill and screw guide of FIG. 1 with the screw in isometric projection.

To allow for the insertion of a screw 18 within the bone 9, the drill guide 14 is removed from the cannula 11 as best seen by referring now to the screw-drill guide assembly 10 depicted in FIG. 2. The cannula 11 remains temporally affixed to the bone 9 with the handle 8 extending from the cylinder 12 in the same exact position. The screw 18 defines a threaded shaft 19 having a tapered end 19A for threadingly engaging the aperture 9A formed within the bone 9 by means of the drill 17 in the manner described earlier with reference to FIG. 1 and a cylindrical screw head 20 defining a hexagonal opening or slot 20A for receiving a screw driver.

The outer diameter D19 of the threaded shaft 19 of screw 18 is arranged for slightly greater than clearance relation with the internal opening 13 defining an internal diameter D11 while the outer diameter D20 of the screw head 20 is arranged for exact clearance relation with the internal diameter D11 of the internal opening 13 within the cylinder 12 of the cannula 11. The clearance relation between the internal diameter D11 of the cannula 11 and the outer diameter D20 of the screw head 20 is an important feature of the invention. By this arrangement, the screw 18 is guided within the cannula by virtue of the screw head, per se, eliminating the need for an extra screw guide as called for in previous drill guide assemblies.

What is claimed is:

1. A combination drill and screw guide comprising in combination: a hollow cannula cylinder having predetermined cannula cylinder internal diameter; said cannula cylinder including a serrated bottom end to said cannula cylinder for promoting insertion of said bottom end within a drillable object, a hollow drill guide cylinder having a predetermined drill guide cylinder outer diameter and a drill guide cylinder inner diameter, said drill guide cylinder outer diameter being sized for clearance fit relation with said cannula cylinder inner diameter, whereby said drill guide cylinder is removably insertable within said cannula cylinder;

a solid drill cylinder having a predetermined bladed drill cylinder outer diameter, said drill cylinder outer diameter being sized for clearance fit relation with said cannula cylinder inner diameter, whereby said drill cylinder is removably insertable within said drill guide cylinder; and a solid screw threaded cylinder having a predetermined solid screw threaded cylinder predetermined diameter and a screw head at one end thereof, said screw head having a predetermined outer diameter greater than said threaded cylinder diameter, said screw head outer diameter being sized for clearance fit relation with said cannula cylinder inner diameter whereby said cannula inner cylinder guides said screw head when said drill guide cylinder is removed from said cannula cylinder and said screw is inserted therein.

2. The combination drill and screw guide of claim 1 including a handle extension attached to said cannula cylinder for manual rotation thereof.

3. A method for guiding a drill and a screw within an object comprising the steps of:

providing a hollow cannula cylinder having predetermined cannula cylinder internal diameter, said cannula cylinder including a serrated end;

positioning said cannula cylinder serrated end in abutment with a drillable object;

rotating said cannula cylinder to move said serrated end partially within said drillable object.

inserting a hollow drill guide cylinder within said cannula cylinder, said drill guide cylinder having a predetermined drill guide cylinder outer diameter and a drill guide cylinder inner diameter, said drill guide cylinder outer diameter being sized for clearance fit relation with said cannula cylinder inner diameter;

rotating said solid drill cylinder to form an aperture within said drillable object; inserting a hollow drill guide cylinder within said cannula cylinder, said drill guide cylinder having a predetermined drill guide cylinder outer diameter and a drill guide cylinder inner diameter, said drill guide cylinder outer diameter being sized for clearance fit relation with said cannula cylinder inner diameter;

removing said solid drill cylinder and said hollow drill guide cylinder from said cannula cylinder;

inserting a solid screw threaded cylinder within said cannula inner cylinder guide into said drillable object aperture, said solid screw cylinder having a predetermined solid screw threaded cylinder predetermined diameter and a screw head at one end thereof, said screw head having a predetermined outer diameter greater than said threaded cylinder diameter, said screw head outer diameter being sized for clearance fit relation with said cannula cylinder inner diameter; and removing said cannula guide from abutment with said drillable object.

* * * * *